United States Patent [19]
Lin et al.

[11] Patent Number: 5,804,139
[45] Date of Patent: Sep. 8, 1998

[54] TWO-STEP STERILIZATION PROCESS USING LIQUID STERILANT

[75] Inventors: Szu-Min Lin, Laguna Hills; Paul Taylor Jacobs, Trabuco Canyon, both of Calif.

[73] Assignee: Ethicon, Inc., Somerville, N.J.

[21] Appl. No.: 770,867

[22] Filed: Dec. 20, 1996

[51] Int. Cl.⁶ .................................. A61L 2/08; A61L 9/00
[52] U.S. Cl. ................................. 422/27; 422/28; 422/31; 422/32; 422/33
[58] Field of Search .................... 422/27, 28, 31, 422/32, 33

[56] References Cited

U.S. PATENT DOCUMENTS

| | | | |
|---|---|---|---|
| 5,246,663 | 9/1993 | Ohama et al. | 422/30 |
| 5,417,676 | 5/1995 | Watanabe et al. | 422/28 |
| 5,468,448 | 11/1995 | Nicolson et al. | 422/30 |
| 5,667,753 | 9/1997 | Jacobs et al. | 422/29 |

*Primary Examiner*—Edward J. Cain

[57] ABSTRACT

A method sterilizes a device having a diffusion restricted area and a non-diffusion restricted area. The method includes the steps of contacting the device with liquid sterilant outside or inside a sterilization chamber fluidly connected to at least one pump, placing the device in the chamber (before or after the contacting step), bringing the pressure of the chamber to a first pressure range at which liquid sterilant is vaporized from the non-diffusion restricted area to sterilize the non-diffusion restricted area, and bringing the pressure of the chamber to a second pressure range at which the liquid sterilant is vaporized from the diffusion restricted area to sterilize the diffusion restricted area. The minimum pressure in the second pressure range is lower than the maximum pressure in the first pressure range.

17 Claims, 2 Drawing Sheets

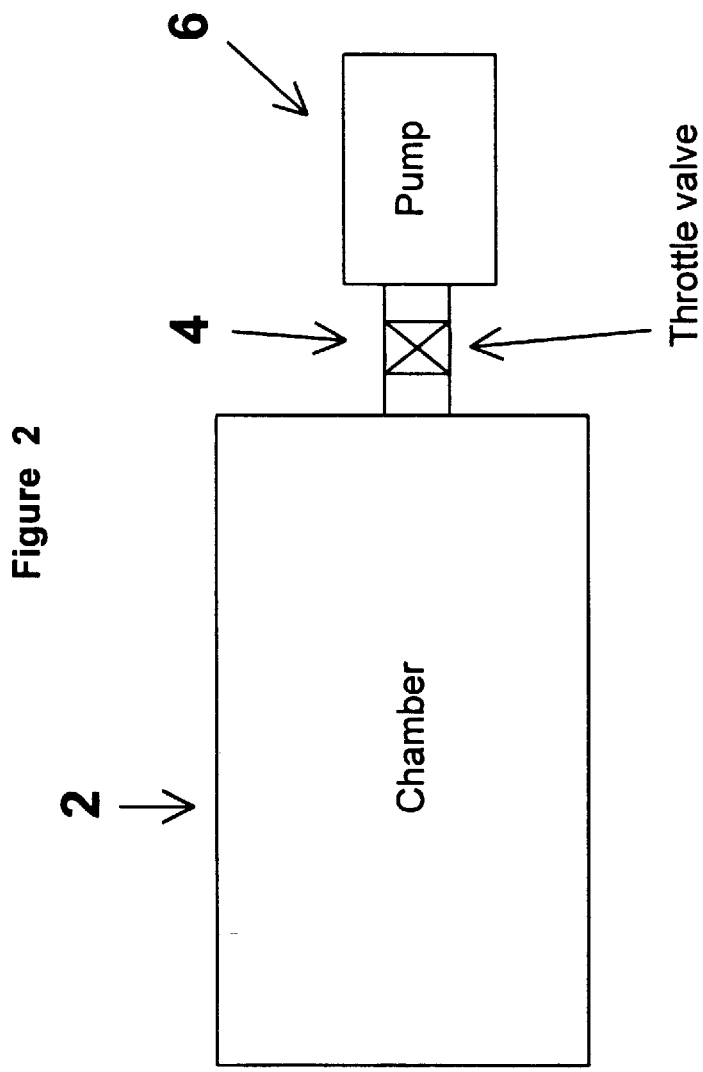

TWO-STEP STERILIZATION PROCESS USING LIQUID STERILANT

FIELD OF THE INVENTION

The present invention relates to a process for sterilization of medical instruments using a liquid sterilant. More particularly, the invention relates to a process in which sterilization is achieved by vaporizing hydrogen peroxide at two different pressure ranges.

BACKGROUND OF THE INVENTION

Medical instruments have traditionally been sterilized using either heat, such as is provided by steam, or a chemical, such as formaldehyde or ethylene oxide in the gas or vapor state. Each of these methods has its drawbacks. Many medical devices such as fiberoptic devices, endoscopes, power tools, etc., are sensitive to heat, moisture or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization time undesirably long.

Sterilization using liquid hydrogen peroxide solution has been found to require high concentrations of sterilant, extended exposure time and/or elevated temperatures. However, sterilization using hydrogen peroxide vapor has been shown to have some advantages over other chemical sterilization processes (see, e.g., U.S. Pat. Nos. 4,169,123 and 4,169,124). The combination of hydrogen peroxide with a plasma provides certain additional advantages, as disclosed in U.S. Pat. No. 4,643,876. The sterilization of articles containing diffusion-restricted areas, such as long narrow lumens, presents a special challenge. Methods that use hydrogen peroxide vapor that has been generated from an aqueous solution of hydrogen peroxide have certain disadvantages. One disadvantage is that because water has a higher vapor pressure than hydrogen peroxide, it will vaporize faster. Another disadvantage is that because of its lower molecular weight, water will diffuse faster than hydrogen peroxide in the vapor state. Because of these physical properties, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into diffusion-restricted areas, such as small crevices and long narrow lumens. This problem cannot be addressed by removing water from the aqueous solution and using more concentrated hydrogen peroxide because, among other reasons, hydrogen peroxide solutions greater than 65% by weight can be hazardous due to their oxidizing potential.

U.S. Pat. No. 4,952,370 discloses a sterilization process in which aqueous hydrogen peroxide vapor is first condensed on the article to be sterilized, followed by application of a vacuum to the sterilization chamber to evaporate the water and hydrogen peroxide from the article. This method is suitable for surface sterilization, but not for sterilization of diffusion-restricted areas such as long narrow lumens because it depends on the diffusion of hydrogen peroxide vapor into the lumen to effect sterilization.

U.S. Pat. No. 4,943,414 discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the existing pressure differential, increasing the sterilization rate for lumens, but has the disadvantage that the vessel needs to be attached to each lumen to be sterilized. In addition, water is vaporized faster and precedes the hydrogen peroxide vapor into the lumen.

In U.S. Pat. No. 5,492,672, there is disclosed a process for sterilizing narrow lumens. This process uses a multicomponent sterilant vapor and requires successive alternating periods of flow of sterilant vapor and discontinuance of such flow. A complex apparatus is used to accomplish the method. Because flow through of vapor is used, closed end lumens are not readily sterilized in the process.

Thus, there remains a need for a simple and effective method of vapor sterilization of articles having areas where diffusion of these vapors is restricted, such as long narrow lumens.

SUMMARY OF THE INVENTION

One embodiment of the present invention is a method for sterilizing a device having a diffusion restricted area and a non-diffusion restricted area comprising the steps of:

contacting the device with liquid sterilant outside or inside a sterilization chamber fluidly connected to at least one pump;

placing the device in the chamber before or after the contacting step;

bringing the pressure of the chamber to a first pressure range at which liquid sterilant is vaporized from the non-diffusion restricted area to sterilize the non-diffusion restricted area;

bringing the pressure of the chamber to a second pressure range at which the liquid sterilant is vaporized from the diffusion restricted area to sterilize the diffusion restricted area, wherein the minimum pressure in the second pressure range is lower than the maximum pressure in the first pressure range.

Preferably, the first pressure range is 20 to 760 torr; more preferably, the first pressure range is 20 to 80 torr; most preferably, the first pressure range is 40–50 torr. Advantageously, the second pressure range is 1–30 torr; more advantageously, the second pressure range is 5–10 torr. In one aspect of this preferred embodiment, the device includes a diffusion-restricted environment. Preferably, the device is a medical instrument with a lumen having an interior and an exterior surface. Advantageously, the sterilant is hydrogen peroxide. According to another aspect of this preferred embodiment, the chamber is at a set temperature and wherein the first pressure is greater than the vapor pressure of the sterilant at the set temperature. Preferably, the pressure of the chamber is maintained constant at the first pressure for a time period sufficient to sterilize the non-diffusion restricted area. Advantageously, the pressure of the chamber is maintained constant at the second pressure for a time period sufficient to sterilize the diffusion restricted area. The pressure of the chamber may be permitted to increase after reaching the first or second pressure range as a result of vaporization of the sterilant within said chamber. Alternatively, the pressure of the chamber is permitted to decrease after reaching the first or second pressure through pumping of said chamber at a rate slower than used to decrease the pressure between said first and second pressure ranges. Preferably, the contacting step is with liquid or condensed vapor. The method can also include the steps of bringing the pressure to a third pressure lower than the second pressure to remove residual sterilant and/or exposing the device to plasma to remove residual sterilant or enhance sterilization efficacy.

BRIEF DESCRIPTION OF THE DRAWINGS

FIG. 2 is a schematic diagram of a chamber, pump and throttle valve for use in the hydrogen peroxide sterilization process of the invention.

DETAILED DESCRIPTION OF THE PREFERRED EMBODIMENTS

1. Introduction

Figure 1:
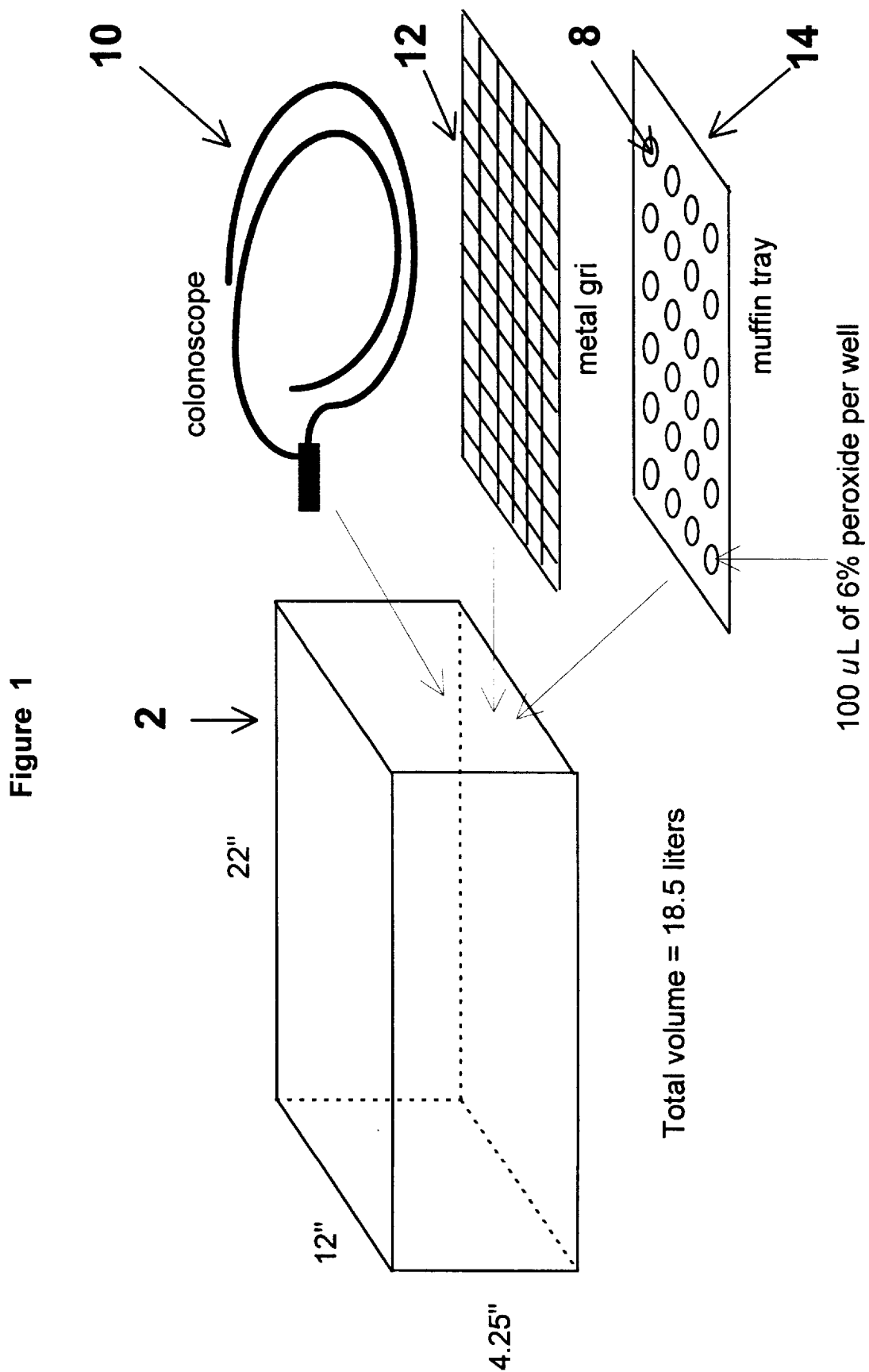
FIG. 1 is a schematic diagram of a chamber and accessories suitable for use in the hydrogen peroxide sterilization process of the invention.

Sterilizing the inside of lumened devices has always posed a challenge to sterilization systems. Applicants' copending U.S. application Ser. No. 08/628,965, the entire contents of which are hereby incorporated by reference, discloses a method of hydrogen peroxide vapor sterilization of diffusion-restricted environments, such as long narrow lumens, at pressures less than the vapor pressure of hydrogen peroxide by pretreating the article to be sterilized with a dilute solution of hydrogen peroxide prior to exposure to a vacuum. One possible approach is to create a diffusion restricted vacuum chamber and to vaporize liquid sterilant within the chamber. Depending upon the size of the diffusion restricted area and the pressure at which the sterilization is performed, it may take too long to evacuate the system. Achieving rapid sterilization of lumened devices or other diffusion restricted articles at low temperatures and low concentrations of sterilant represents an even greater challenge.

An apparatus useful in the process of the present invention is shown schematically in FIGS. 1 and 2 and comprises a chamber 2, a throttle valve 4 and a pump 6. In FIG. 2, the chamber 2 is attached to the pump 6 by the throttle valve 4. The valve 4 can be controlled either automatically to maintain the pressure or manually to maintain a constant pump-down rate. In the automatic mode of operation, the throttle valve 4 opens based on the pressure in the chamber via a pressure transducer and valve controller. Such valves are commercially available from, for example, MKS (Andover, Md.). In this process a dilute, aqueous solutions of hydrogen peroxide is placed in wells 8 as shown in FIG. 1. As the pressure in the sterilization chamber 2 is reduced, the hydrogen peroxide vaporizes and contacts the surface to be sterilized (i.e., colonoscope 10 in FIG. 1) which is placed on metal grid 12 which rests on tray 14. In a preferred embodiment, the tray can be configured with a plurality of wells designed to retain a known volume of liquid sterilant. In one embodiment, the volume of sterilization chamber 2 is about 18.5 liters and its dimensions are about 22" (55.9 cm)×4.25" (10.8 cm)×12" (30.5 cm).

Hydrogen peroxide can be introduced into the chamber as a liquid. In a preferred embodiment, hydrogen peroxide is introduced as a vapor and the chamber parameters are changed so that the vapor condenses as a liquid on the surface of an article to be sterilized. Such changes include increasing the pressure.

The aqueous solutions of hydrogen peroxide can be relatively dilute, e.g. as low as 1–6% peroxide by weight, since sterilization is not achieved through contact with the hydrogen peroxide solution, but rather is achieved at low temperatures and in short periods of time upon exposure to hydrogen peroxide under vacuum. The method of the present invention is particularly effective with articles having inaccessible or hard-to-reach places. Such articles include long, narrow lumens, hinges and other articles having spaces where diffusion of vapors is restricted. Although hydrogen peroxide is used in the examples described herein, the use of other liquid sterilants are also contemplated. Preferred sterilants have vapor pressures lower than the vapor pressure of the solvent in which they are provided. Such sterilants include, for example, aqueous peracetic acid solution and aqueous glutaraldehyde solution.

At the end of the process, deep vacuum can be used to remove residual sterilant. A plasma can also be used to remove residual sterilant and to enhance sterilization efficacy.

The method of the present invention is described below. This invention results from our discovery that different pressures are optimally used to sterilize the exterior of diffusion-restricted articles than the interior thereof. As used herein, a "diffusion-restricted" area refers to any one or more of the following properties: (1) the ability of the area of an article placed within the sterilization system of the present invention to retain 0.17 mg/L or more hydrogen peroxide solution after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the hydrogen peroxide solution placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

2. Sterilization of Exterior

To evaluate the sterilization efficacy of hydrogen peroxide vapor generated from 6% hydrogen peroxide solution at different pressures on the exterior surface of an article to be sterilized, a biological challenge consisting of $2.3 \times 10^6$ *Bacillus stearothermophilus* (Bst) spores was placed in uncovered petri dishes or on the insertion tube of a CF10 colonoscope (Olympus). Four scalpel blades were used per cycle, two in the petri dish and two on the colonoscope. The temperature of the chamber was 45° C. The pressure varied from 200 torr to 1 torr by controlling the valve in automatic mode. 2400 µl in 50 drops of 6% peroxide were used as shown in FIG. 1. The blades were removed and tested for sterility. The results of this testing is present in Table 1 as a ratio of the number of inoculated blades which remain contaminated after treatment over the number of inoculated blades tested.

TABLE 1

| | Sporicidal Activity (positives/samples) | | | |
|---|---|---|---|---|
| | 5 minutes | | 10 minutes | |
| Pressure (torr) | In uncovered petri dish | On insertion tube of colonoscope | In uncovered petri dish | On insertion tube of colonoscope |
| 200 | 1/2 | 2/2 | 0/2 | 0/2 |
| 175 | 0/2 | 2/2 | 0/2 | 0/2 |
| 150 | 0/2 | 2/2 | 0/2 | 0/2 |
| 125 | 0/2 | 2/2 | 0/2 | 0/2 |
| 100 | 0/2 | 2/2 | 0/2 | 0/2 |
| 90 | 0/2 | 2/2 | 0/2 | 0/2 |
| 80 | 0/2 | 1/2 | 0/2 | 0/2 |
| 70 | 0/2 | 1/2 | 0/2 | 0/2 |
| 60 | 0/2 | 1/2 | 0/2 | 0/2 |
| 50 | 0/2 | 0/2 | 0/2 | 0/2 |
| 40 | 0/2 | 0/2 | 0/2 | 0/2 |
| 30 | 0/2 | 2/2 | 0/2 | 1/2 |
| 25 | 0/2 | 2/2 | 0/2 | 2/2 |
| 20 | 0/2 | 2/2 | 0/2 | 2/2 |
| 15 | 0/2 | 2/2 | 0/2 | 2/2 |
| 10 | 1/2 | 2/2 | 0/2 | 2/2 |
| 5 | 2/2 | 2/2 | 2/2 | 2/2 |
| 1 | 2/2 | 2/2 | 2/2 | 2/2 |

As shown in the table, if the pressure is too low (5 torr or less), the majority of peroxide vaporizes immediately and is removed during evacuation. Thus, less peroxide is available to sterilize the blades. Under the test conditions, the optimal pressure for the 5 minute time period is about 40–50 torr. With 10 minutes exposure, sterilization can be achieved at pressures up to about 200 torr. It appears to take longer to vaporize peroxide at higher pressures. The vapor pressure of hydrogen peroxide under these conditions is about 80–90 torr, thus sterilization can be achieved at pressures higher than the vapor pressure of hydrogen peroxide. The blades on the insertion tube may simulate the most difficult areas to be sterilized in the system because the insertion tube tends to absorb peroxide, leaving less available for sterilization of the blades placed thereon.

The exterior of the article can also be effectively sterilized when performed at atmospheric pressure. In order to confirm this, two scalpel blades were each inoculated with $2.3 \times 10^6$ Bst spores (two SS blades per cycle), placed in uncovered petri dishes, placed in the chamber and exposed to 48 drops×50 $\mu$l/drop of 6% hydrogen peroxide at 60° C. at atmospheric pressure. Both blades were sterilized after 30 minutes exposure under these conditions.

3. Interior Sterilization

To determine the efficacy of the liquid/vapor process on the inside surfaces of an article to be sterilized, polytetrafluoroethylene (PTFE) lumens containing Bst spores were used. The effects of lumen length, internal diameter and amount of peroxide in the lumen on sterilization were investigated. PTFE lumens were loaded with a stainless steel coupon at the center of the lumen. A stainless steel coupon consists of a piece of scalpel blade cut from the proximal end of the blade having dimensions of about 2 mm×4 mm. Sterilization parameters were: 45° C., 48 drops×50 $\mu$l per drop 6% peroxide; $8.8 \times 10^5$ Bst per coupon and 10 minute exposure. Peroxide was either absent from the lumen or present about 1 cm or more away from the coupon on both sides thereof. The length of the lumen was 20, 50, 100 or 200 cm. The internal diameter of the lumen was 2.38 or 4.76 mm. The results for the lumens not containing additional peroxide in the lumen are shown in Table 2A.

TABLE 2A

| Length of Lumen | I.D. of Lumen | Amount of peroxide in the lumen | Presence of Spores | | | | |
|---|---|---|---|---|---|---|---|
| | | | 50 torr | 30 torr | 10 torr | 5 torr | 1 torr |
| 20 cm | 2.38 mm | 0 | − | − | + | + | + |
| | 4.76 mm | 0 | − | − | + | + | + |
| 50 cm | 2.38 mm | 0 | + | + | + | + | + |
| | 4.76 mm | 0 | + | + | + | + | + |
| 100 cm | 2.38 mm | 0 | + | + | + | + | + |
| | 4.76 mm | 0 | + | + | + | + | + |

Because no peroxide was present in the lumen, the only source of peroxide for sterilization of the lumen was from outisde the lumen, such as from wells placed in the sterilization chamber. Thus, diffusion of the peroxide vapor from outside to the inside of the device is required. As shown in Table 2A, these parameters resulted in sterilization of only the shortest lumen tested (20 cm), and only at the highest pressures (30 and 50 torr). Because peroxide vapor is diffusing from outside to inside, when the pressure is too low, very little peroxide is present because most is removed from the chamber at the lower pressures. Without hydrogen peroxide in the lumen, only short lumens can be sterilized at high pressure because the flow of peroxide vapor is from outside to inside. The center of the longer lumens could not be reached by the peroxide vapor diffusing in from the outside source.

TABLE 2B

| Length of Lumen | I.D. of Lumen | Amount of peroxide in the lumen | Presence of Spores | | | | |
|---|---|---|---|---|---|---|---|
| | | | 50 torr | 30 torr | 10 torr | 5 torr | 1 torr |
| 20 cm | 2.38 mm | 2 × 5 $\mu$L | + | + | − | − | + |
| | 4.76 mm | 2 × 5 $\mu$L | − | + | − | − | + |
| 50 cm | 2.38 mm | 2 × 5 $\mu$L | + | − | − | − | + |
| | 4.76 mm | 2 × 5 $\mu$L | − | − | − | − | + |
| 100 cm | 2.38 mm | 2 × 2.5 $\mu$L | + | + | − | − | − |
| | | 2 × 5 $\mu$L | + | + | − | − | − |
| | 4.76 mm | 2 × 2.5 $\mu$L | − | − | − | − | − |
| | | 2 × 5 $\mu$L | + | + | − | − | − |
| 200 cm | 2.38 mm | 2 × 2.5 $\mu$L | + | − | − | − | − |
| | | 2 × 5 $\mu$L | + | + | − | − | − |
| | 4.76 mm | 2 × 2.5 $\mu$L | + | − | − | − | − |
| | | 2 × 5 $\mu$L | + | + | − | − | − |

The results for the lumens containing additional peroxide are shown in Table 2B. The peroxide was placed about 1 cm away from the coupon on both sides thereof. This method was much more effective in sterilizing the coupons contained within the lumens. It is noted that the 20 cm lumen at 30 and 50 torr contained spores in the 2.38 mm I.D. lumen while the previous table shows that no spores were present under these conditions. While not wishing to be bound by any particular explanation of these results, it is believed that these results are due to the presence of additional water vapor which prevents peroxide from diffusing from outside to inside. The 4.76 mm tube is large enough that the peroxide is not prevented from diffusing from outside to inside. Sterilization can occur at 50 torr because the lumen is large enough. 5 torr and 10 torr consistently provide good efficacy results with hydrogen peroxide in the lumen with the test samples in the lumen. Thus, under the test conditions at 45° C., the optimal pressures for hydrogen peroxide sterilization of the interior of an article (5–10 torr) is different from those for sterilization of the exterior of an article (40–50 torr).

Another experiment examined the effects of exposure time, lumen I.D., amount of peroxide and distance between peroxide and the coupon. The pressure was 5 torr and the length of the Teflon lumen was 200 cm.

TABLE 2C

| Exposure Time | I.D. of Lumen | Amount of Peroxide in the Lumen | Presence of Spores | | |
|---|---|---|---|---|---|
| | | | 1 cm away | 10 cm away | 20 cm away |
| 5 min | 2.38 mm | 2 × 2.5 µL | − | − | − |
| | | 2 × 5.0 µL | − | + | + |
| | 4.76 mm | 2 × 2.5 µL | − | − | − |
| | | 2 × 5.0 µL | − | − | − |
| 10 min | 2.38 mm | 2 × 2.5 µL | − | − | − |
| | | 2 × 5.0 µL | − | − | − |
| | 4.76 mm | 2 × 2.5 µL | − | − | − |
| | | 2 × 5.0 µL | − | − | − |

As shown in Table 2C, the peroxide source could be placed 1 cm, 10 cm, or 20 cm from the coupon and still result in effective sterilization thereof. The one exception was the 5 minute exposure time, 2.38 mm I.D., 2×5.0 µl peroxide. This may be due to vaporization of water which impedes access of peroxide inside the narrower lumen. Small lumens require longer times to vaporize more peroxide solution.

4. Two-step process

In view of the different optimal pressures for sterilizing the inside and outside of diffusion-restricted articles, we have developed a two-step process for rapidly sterilizing both the interior and exterior of articles. Depending on the temperature, concentration and amount of hydrogen peroxide, the first step is performed at a first pressure range which can be as high as atmospheric pressure and as low as about 20 torr. The second pressure range is typically between 1 and about 30 torr, preferably between about 5 and 10 torr. In a preferred embodiment upon reaching the first or second pressure ranges in the two-step process, the valve between the pump and the chamber is closed to allow peroxide vaporization which increases the pressure. In another embodiment, the first or second pressure ranges occur through gradual evacuation of the chamber starting at a pressure at a higher end of the range (i.e. the first and second pressures are not linearly maintained). Optionally, a final evacuation step may be rapidly performed to remove condensed residual hydrogen peroxide at a very low pressure (0.1–5 torr). A plasma can also be used for this purpose or to help in the sterilization process.

During the sterilization at each of the first and second pressure ranges, the valve to the chamber can be set to control the pressure of the chamber to remain constant. Alternatively, and more preferably, the valve can be closed, so as to permit the pressure within the chamber to increase as a result of vaporization of the sterilant. Allowing the pressure to so rise will permit additional sterilant vapor to contact the article to be sterilized. In still another alternative, the valve can be set to continue decreasing the pressure of the chamber, albeit at a slower rate.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A method for sterilizing a device having a diffusion restricted area and a non-diffusion restricted area comprising the steps of:

contacting said device with liquid sterilant outside or inside a sterilization chamber fluidly connected to at least one pump;

placing said device in said chamber before or after the contacting step;

bringing the pressure of said chamber to a first pressure range at which liquid sterilant is vaporized from the non-diffusion restricted area to sterilize the non-diffusion restricted area; and bringing the pressure of said chamber to a second pressure range at which the liquid sterilant is vaporized from the diffusion restricted area to sterilize the diffusion restricted area, wherein the minimum pressure in the second pressure range is lower than the maximum pressure in the first pressure range.

2. The method of claim 1, wherein said first pressure range is 20 to 760 torr.

3. The method of claim 2, wherein said first pressure range is 20 to 80 torr.

4. The method of claim 3, wherein said first pressure range is 40–50 torr.

5. The method of claim 1, wherein said second pressure range is 1–30 torr.

6. The method of claim 5, wherein said second pressure range is 5–10 torr.

7. The method of claim 1, wherein said device includes a diffusion-restricted environment.

8. The method of claim 7, wherein said device is a medical instrument with a lumen having an interior and an exterior surface.

9. The method of claim 1, wherein said sterilant is hydrogen peroxide.

10. The method of claim 1, wherein the chamber is at a set temperature and wherein the first pressure is greater than the vapor pressure of said sterilant at the set temperature.

11. The method of claim 1, wherein the pressure of the chamber is maintained constant at said first pressure for a time period sufficient to sterilize the non-diffusion restricted area.

12. The method of claim 1, wherein the pressure of the chamber is maintained constant at said second pressure for a time period sufficient to sterilize the diffusion restricted area.

13. The method of claim 1, wherein the pressure of the chamber is permitted to increase after reaching the first or second pressure range as a result of vaporization of said sterilant within said chamber.

14. The method of claim 1, wherein the pressure of the chamber is permitted to decrease after reaching the first or second pressure through pumping of said chamber at a rate slower than used to decrease the pressure between said first and second pressure ranges.

15. The method of claim 1, wherein said contacting step comprises application of liquid or condensed vapor.

16. The method of claim 1, additionally comprising bringing the pressure to a third pressure lower than the second pressure to remove residual sterilant.

17. The method of claim 1, additionally comprising exposing said device to plasma to remove residual sterilant or enhance sterilization efficacy.

* * * * *